United States Patent [19]
Sundeen et al.

[11] Patent Number: 4,904,775
[45] Date of Patent: Feb. 27, 1990

[54] HETEROAROYLHYDRAZIDE DERIVATIVES OF MONOCYCLIC BETA-LACTAM ANTIBIOTICS

[75] Inventors: Joseph E. Sundeen, Yardley, Pa.; Peter H. Ermann, Donaustauf, Fed. Rep. of Germany

[73] Assignee: E. R. Squibb & Sons, Inc., Princeton, N.J.

[21] Appl. No.: 194,355

[22] Filed: May 16, 1988

[51] Int. Cl.$^4$ .................. C07D 417/14; C07D 241/44; C07D 491/048; C07D 417/12

[52] U.S. Cl. ..................................... 540/363; 540/357; 540/360; 540/364; 544/354; 544/345; 546/92; 548/194; 549/439; 549/434

[58] Field of Search ................ 540/363, 364, 360, 357

[56] References Cited

U.S. PATENT DOCUMENTS

| | | | |
|---|---|---|---|
| 4,217,453 | 8/1980 | Christensen et al. | 544/373 |
| 4,224,336 | 9/1980 | Christensen et al. | 546/272 |
| 4,610,824 | 9/1986 | Truner | 540/355 |

FOREIGN PATENT DOCUMENTS

| | | |
|---|---|---|
| 0254495 | 1/1988 | European Pat. Off. . |
| 0010426 | 4/1988 | European Pat. Off. . |

OTHER PUBLICATIONS

Mochida, et al.; Aminothiazolylglycyl Derivatives of Carbacephem Antibiotics, Feb., 1987, pp. 182–189, Journal of Antibiotics.

Mochida, et al.; Aminothiazolylglycol Derivatives of Carbacephems, Jan., 1987, pp. 14–21, Journal of Antibiotics.

Primary Examiner—Mark L. Berch
Attorney, Agent, or Firm—Donald J. Barrack; Stephen Venetainer

[57] ABSTRACT

Compounds having the formula

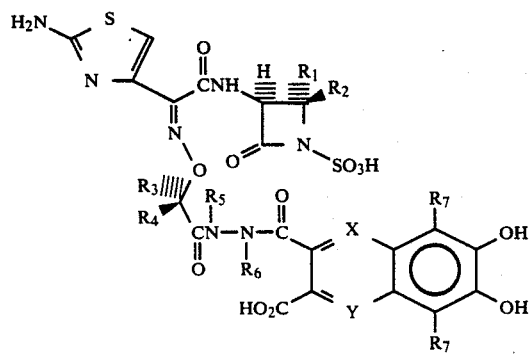

and pharmaceutically acceptable salts thereof and possessing antibacterial activity, and intermediates to compounds of formula I having the formula

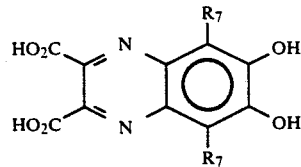

26 Claims, No Drawings

HETEROAROYLHYDRAZIDE DERIVATIVES OF MONOCYCLIC BETA-LACTAM ANTIBIOTICS

BRIEF DESCRIPTION OF THE INVENTION

Compounds having the formula

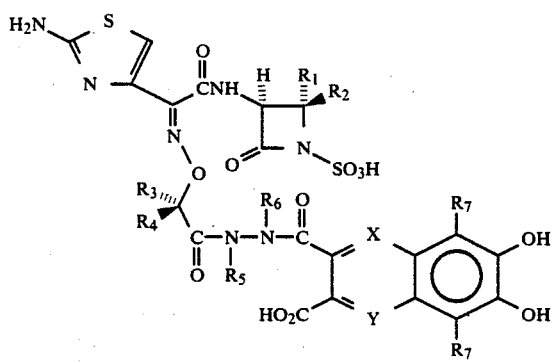

and pharmaceutically acceptable salts thereof and possessing antibacterial activity. In formula I, and throughout the specification, the symbols are as defined below.

$R_1$ and $R_2$ are the same or different and each is hydrogen, alkyl, alkenyl, alkynyl, cycloalkyl, phenyl, substituted phenyl or a 4, 5, 6 or 7-membered heterocycle (hereinafter referred to as $R_a$), or one of $R_1$ and $R_2$ is hydrogen and the other is azido, halomethyl, dihalomethyl, trihalomethyl, alkoxycarbonyl, 2-phenylethenyl, 2-phenylethynyl, carboxyl, —$CH_2X_1$ [wherein $X_1$ is azido, amino (—$NH_2$), hydroxy, carboxyl, alkoxycarbonyl, alkanoyloxy, phenylcarbonylamino, (substituted phenyl)carbonylamino, alkylsulfonyloxy, phenylsulfonyloxy, (substituted phenyl)sulfonyloxy, phenyl, substituted phenyl, cyano,

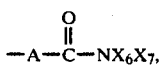

—$S$—$X_2$, or —$O$—$X_2$ (wherein A, $X_2$, $X_6$ and $X_7$ are as hereinafter defined)], —$S$—$X_2$ or —$O$—$X_2$ [wherein $X_2$ is alkyl, substituted alkyl, phenyl, substituted phenyl, phenylalkyl, (substituted phenyl)alkyl, alkanoyl, substituted alkanoyl, phenylalkanoyl, (substituted phenyl)alkanoyl, phenylcarbonyl, (substituted phenyl)carbonyl, or heteroarylcarbonyl], and in the case of when $X_1$ is O—$X_2$ then $X_2$ can also be alkylideneamino, alkanoylamino, carboxyalkylideneamino, alkylsulphonylamino, alkoxycarbonylalkylsulphonylamino or N,N-cyclodialkanoylamino,

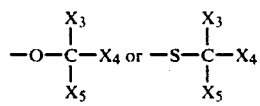

[wherein one of $X_3$ and $X_4$ is hydrogen and the other is hydrogen or alkyl, or $X_3$ and $X_4$ when taken together with the carbon atom to which they are attached form a cycloalkyl group; and $X_5$ is formyl, alkanoyl, phenylcarbonyl, (substituted phenyl)carbonyl, phenylalkylcarbonyl, (substituted phenyl)alkylcarbonyl, carboxyl, alkoxycarbonyl, aminocarbonyl

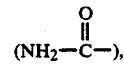

(substituted amino)-carbonyl, or cyano (—C≡N)], or

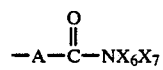

[wherein A is —CH=CH—, —$(CH_2)_m$—, —$(CH_2)_m$—NH—, or —$CH_2$—S—$CH_2$—, m is 0, 1 or 2, and $X_6$ and $X_7$ are the same or different and each is hydrogen, alkyl, phenyl or substituted phenyl, or $X_6$ is hydrogen and $X_7$ is amino, substituted amino, alkanoylamino or alkoxy, or $X_6$ and $X_7$ when taken together with the nitrogen atom to which they are attached form a 4, 5, 6 or 7-membered heterocycle];

$R_3$ and $R_4$ are the same or different and each is hydrogen or alkyl or $R_3$ and $R_4$ together with the carbon atom to which they are attached are cycloalkyl;

$R_5$ and $R_6$ are the same or different and each is hydrogen or alkyl or $R_5$ and $R_6$ taken together with the nitrogen atoms to which they are attached form a 1,2-diazacylobutane, 1,2-diazacyclopentane, 1,2-diazacyclohexane, or 1,2-diazacycloheptane ring.

$R_7$ is hydrogen, fluorine, chlorine or bromine.

X is a nitrogen atom or CH;

Y is a nitrogen atom or CH;

provided that either X or Y is always a nitrogen atom;

Listed below are definitions of various terms used to describe the β-lactams of this invention. These definitions apply to the terms as they are used throughout the specification (unless they are otherwise limited in specific instances) either individually or as part of a larger group.

The terms "alkyl" and "alkoxy" refer to both straight and branched chain groups. Those groups having 1 to 10 carbon atoms are preferred.

The term "cycloalkyl" refers to cycloalkyl groups having 3,4,5,6 or 7 carbon atoms.

The term "substituted alkyl" refers to alkyl groups substituted with one or more (preferably 1, 2 or 3) azido, amino (—$NH_2$), halogen, hydroxy, carboxy, cyano, alkoxycarbonyl, aminocarbonyl, alkanoyloxy, alkoxy, phenyloxy, (substituted phenyl)oxy, $R_a$-oxy, mercapto, alkylthio, phenylthio, (substituted phenyl)thio, alkylsulfinyl, or alkylsulfonyl groups.

The terms "alkanoyl", "alkenyl", and "alkynyl" refer to both straight and branched chain groups. Those groups having 2 to 10 carbon atoms are preferred.

The term "substituted alkanoyl" refers to alkyl groups substituted with one or more (preferably 1, 2 or 3) azido, amino (—$NH_2$), halogen, hydroxy, carboxy, cyano, alkoxycarbonyl, aminocarbonyl, alkanoyloxy, alkoxy, phenyloxy, (substituted phenyl)oxy, mercapto, alkylthio, phenylthio, (substituted phenyl)thio, alkylsulfinyl or alkylsulfonyl groups.

The term "substituted phenyl" refers to a phenyl group substituted with 1, 2 or 3 amino (—$NH_2$), halogen, hydroxyl, trifluoromethyl, alkyl (of 1 to 4 carbon atoms), alkoxy (of 1 to 4 carbon atoms), alkanoyloxy, aminocarbonyl, or carboxy groups.

The expression "a 4,5,6 or 7-membered heterocycle" (referred to as "$R_a$") refers to substituted and unsubstituted, aromatic and non-aromatic groups containing one or more (preferably 1, 2 or 3) nitrogen, oxygen or sulfur atoms. Exemplary substituents are oxo (=O), halogen, hydroxy, nitro, amino, cyano, trifluoromethyl, alkyl of 1 to 4 carbons, alkoxy of 1 to 4 carbons, alkylsulfonyl, phenyl, substituted phenyl, 2-furfurylideneamino

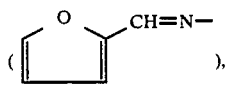

benzylideneamino and substituted alkyl groups (wherein the alkyl group has 1 to 4 carbons). One type of "4,5,6 or 7-membered heterocycle" is the "heteroaryl" group. The term "heteroaryl" refers to those 4,5,6 or 7-membered heterocycles which are aromatic. Exemplary heteroaryl groups are substituted and unsubstituted pyridinyl, furanyl, pyrrolyl, thienyl, 1,2,3-triazolyl, 1,2,4-triazolyl, imidazolyl, thiazolyl, thiadiazolyl, pyrimidinyl, oxazolyl, triazinyl, and tetrazolyl. Exemplary nonaromatic heterocycles (i.e., fully or partially saturated heterocyclic groups) are substituted and unsubstituted azetidinyl, oxetanyl, thietanyl, piperidinyl, piperazinyl, imidazolidinyl, oxazolidinyl, pyrrolidinyl, tetrahydropyrimidinyl, dihyrothiazolyl and hexahydroazepinyl. Exemplary of the substituted 4,5,6 or 7-membered heterocycles are 1-alkyl-3-azetidinyl, 2-oxo-1-imidazolidinyl, 3-alkylsulfonyl-2-oxo-1-imidazolidinyl, 3-benzylideneamino-2-oxo-1-imidazolidinyl, 3-alkyl2-oxo-1-imidazolidinyl, 3-phenyl (or substituted phenyl)-2-oxo-1-imidazolidinyl, 3-benzyl-2-oxo-1-imidazolidinyl, 3-(2-aminoethyl)-2-oxo-1-imidazolidinyl, 3-amino-2-oxo-1-imidazolidinyl, 3-[(alkoxycarbonyl)amino]-2-oxo-1-imidazolidinyl, 3-[2-[(alkoxycarbonyl)-amino]ethyl]-2-oxo-1-imidazolidinyl, 2-oxo-1-pyrrolidinyl, 2-oxo-3-oxazolidinyl, 4-hydroxy-6-methyl-2-pyrimidinyl, 2-oxo-1-hexahydroazepinyl, 2-oxo-3-pyrrolidinyl, 2-oxo-3-tetrahydrofuranyl, 2,3-dioxo-1-piperazinyl, 2,5-dioxo-1-piperazinyl, 4-alkyl-2,3-dioxo-1-piperazinyl, and 4-phenyl-2,3-dioxo-1-piperazinyl.

The term "substituted amino" refers to a group having formula $-NX_8X_9$ wherein $X_8$ is hydrogen, alkyl, phenyl, substituted phenyl, phenylalkyl or (substituted phenyl)alkyl, and $X_9$ is alkyl, phenyl, substituted phenyl, phenylalkyl, (substituted phenyl)alkyl, hydroxy, cyano, alkoxy, phenylalkoxy, or amino ($-NH_2$).

The compounds of this invention form basic salts with inorganic and organic bases which are also within the scope of this invention. Such salts include ammonium salts, alkali metal salts, alkaline earth metal salts, and salts with organic bases such as dicyclohexylamine, benzathine, N-methyl-D-gluccamine, hydrabamine and the like.

The compounds of this invention are pictured as acids. They can also exist, however, as zwitterions (internal or inner salts), and these are also included within the language "pharmaceutically acceptable salts" and the scope of this invention.

DETAILED DESCRIPTION OF THE INVENTION

The β-lactams of formula I, and pharmaceutically acceptable salts thereof, have activity against gram-positive and gram-negative organisms. Of particular interest is the good activity against gram negative organisms in vitro and in vivo exhibited by the compounds of this invention. The compounds of this invention can be used as agents to combat bacterial infections (including urinary tract infections and respiratory infections) in mammalian species, such as domesticated animals (e.g., dogs, cats, cows, horses, and the like) and humans.

For combating bacterial infections in mammals, a compound of this invention can be administered to a mammal in need thereof in an amount of about 1.4 mg/kg/day to about 350 mg/kg/day, preferably about 14 mg/kg/day to about 100 mg/kg/day. All modes of administration which have been used in the past deliver penicillins and cephalosporins to the site of the infection are also contemplated for use with β-lactams of this invention. Such methods of administration include oral, intravenous, intramuscular, and as a suppository.

The compounds of this invention can be prepared by coupling a compound having a formula

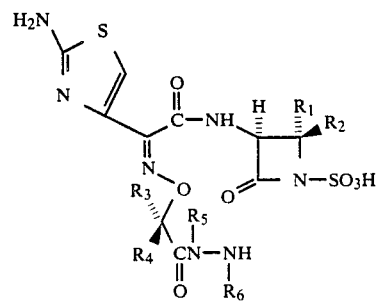

with an anhydride of the formula

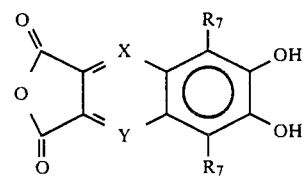

in such solvents as dimethyl formamide or dichloromethane in the presence of a tertiary amine base such as triethylamine or tributylamine.

When X is not Y, two compounds of formula I can be obtained wherein X is nitrogen and Y is CH or X is CH and Y is nitrogen.

The compound of the formula II wherein $R_2$, $R_5$, and $R_6$ are hydrogen and $R_1$, $R_3$ and $R_4$ are methyl is described in the literature; see U.S. Pat. No. 4,610,824.

The compounds of the formula II can be prepared from compounds of the formula

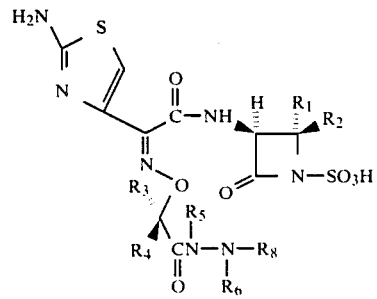

wherein $R_8$ is a protecting group such as (t-butyloxy)-carbonyl, by methods of deprotection well known in the art such as treatment with a strong acid such as trifluoroacetic acid.

The compound of the formula IV can be prepared using a variety of procedures such as described in U.S. Pat. No. 4,610,824. One method utilizes as a starting material the known monocyclic β-lactam antibiotics having the formula

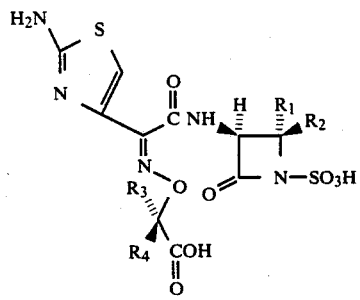

and salts thereof. Compounds of formula V are described in the literature; see, for example, United Kingdom patent application No. 2,071,650, published Sept. 23, 1981. Reaction of a compound of formula V with a hydrazide having the formula

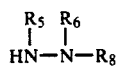

wherein $R_8$ is a protecting group such a (t-butyloxy)carbonyl, in the presence of a coupling agent, yields the desired products of the formula IV. If the starting material of formula V is an inner salt (—$SO_3H$ in the 1-position), it is preferable to first treat the compound with one equivalent of a base (e.g., triethylamine or tributylamine) to form a salt of the sulfonic acid. Preferably, the reaction is run in the presence of a substance capable of forming a reactive intermediate in situ, such as N-hydroxybenzotriazole and/or a catalyst such as N,N-dimethylaminopyridine, using a coupling agent such as dicyclohexylcarbodiimide. Exemplary solvents which can be used for the reaction are dimethylformamide, tetrahydrofuran, dichloromethane or mixtures thereof.

Hydrazine derivatives of formula VI can be prepared from hydrazines of the formula

using methods of amine group protection and deprotection well known in the art, such as reviewed in T. W. Greene, "Protective Groups in Organic Synthesis", John Wiley & Sons, New York, 1981, and E. Gross and J. Meienhofer, "The Peptides: Analysis, Synthesis, Biology; Vol. 3-Protection of Functional Groups in Peptide Synthesis", Academic Press, New York, 1981.

Hydrazine derivatives of formula VII and methods for their preparation, are well known in the literature. Reviews of their synthesis can be found in Smith, "The Chemistry of Open-Chain Organic Nitrogen Compounds", Vols. I and II, Benjamin, Inc., New York, Amsterdam, 1966; Muller, "Methoden der Organischen Chemie" (Houben-Weyl), Vol 10/2, George Thieme Verlag Stuttgart, 1967; Sandler and Karo, "Organic Functional Group Preparations", Vol 1, Academic Press, New York, 1968; and Timberlake and Stowell, "The Chemistry Hydrazo, Azo, and Azoxy Groups", ed. S. Patai, part 1, Interscience, New York, 1975.

Alternatively, compounds of the formula IV can be prepared by acylating a compound having the formula

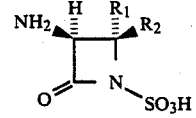

or a salt thereof, with a carboxylic acid having the formula

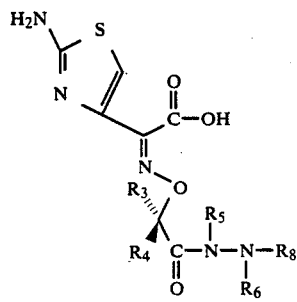

Well-known acylation procedures can be used for the reaction. Exemplary techniques include the use of a carboxylic acid of formula IX or a corresponding carboxylic acid halide or carboxylic acid anhydride. The reaction with a carboxylic acid proceeds most readily in the presence of a coupling agent such as dicyclohexylcarbodiimide and a substance capable of forming a reactive intermediate in situ such as N-hydroxybenzotriazole or N-hydroxysuccinimide.

Compounds of formula IX can be prepared by reacting 2-amino-4-thiazoleglyoxylic acid, which has the formula

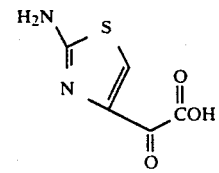

with a compound of the formula

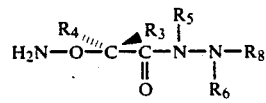

or a salt thereof. The reaction proceeds best in water and in mixtures of water and organic solvents, such a methanol, ethanol, tetrahydrofuran or dioxane.

Reactants of formula XI can be prepared by reacting a compound having the formula

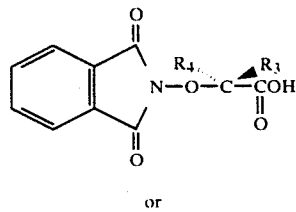

or

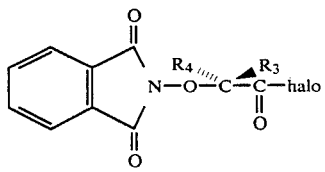

XIII with a hydrazide having the formula

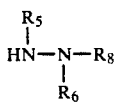

VI to yield the corresponding compound having the formula

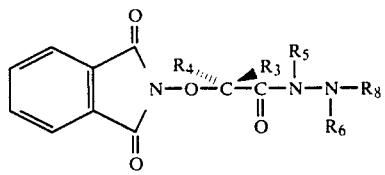

XIV

If an acid reactant of formula XII is used, a suitable coupling agent, such as dicylohexylcarbodiimide, should be present. Alternatively, an acid of formula XII can be activated by formation of a mixed anhydride. If an acid halide derivative of formula XIII is used, a suitable base should be present. The hydrazides of formula XIV can be deprotected using methodology well-known in the art to yield the desired reactants of formula XI. Exemplary deprotecting agents are hydrazine and methylhydrazine.

Alternatively, compounds of the formula II can be prepared by reacting compounds of the formula V with hydrazines of the formula

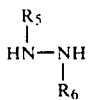

VII wherein $R_5$ and $R_6$ are the same or form a 1,2-diazacyclobutane, 1,2-diazacylopentane, 1,2-diazacyclohexane, or 1,2-diazacycloheptane ring or wherein $R_5$ is alkyl and $R_6$ is hydrogen, in the presence of a coupling agent. Preferably, the reaction is run in the presence of a substance capable of forming a reactive intermediate in situ, such as N-hydroxybenzotriazole and/or a catalyst such as N,N-dimethylaminopyridine, using a coupling agent such as dicylohexylcarbodiimide. Exemplary solvents which can be used for the reaction are dimethylformamide, tetrahydrofuran, dichloromethane, or mixtures thereof.

The compounds of the formula III wherein X and Y are nitrogen are prepared by reacting compounds of the formula

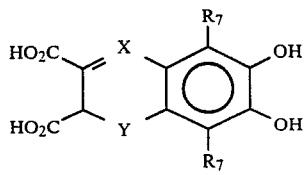

XV wherein X and Y are nitrogen with a dehydrating agent such as dicyclohexylcarbodiimide in a solvent such as dimethylformamide, or by heating with a dehydrating agent such as thionyl chloride or phosphorous oxychloride.

Compounds of the formula XV wherein X and Y are nitrogen are prepared by methods of deprotection well known in the art from compounds of the formula

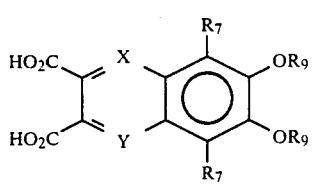

XVI wherein X and Y are nitrogen and $R_9$ is arylmethyl (such as benzyl or p-methoxybenzyl; deprotection can be achieved by heating with a strong acid such as hydrochloric acid, or by hydrogenolysis over a catalyst such as palladium on charcoal), acyl (such as acetyl or propanoyl; deprotection can be achieved by treating with a strong base such as sodium hydroxide in a solvent such as water or methanol), aroyl (such as benzoyl or p-nitrobenzoyl; deprotection can be achieved by treating with a strong base such as sodium hydroxide in a solvent such as water or methanol), or wherein $R_9$ taken together form a cyclic ketal (such as 2,2-propylidene or cycloghexylidene; deprotection can be achieved by heating with a strong acid such as hydrochloric acid).

Compounds of the formula XV wherein X and Y are nitrogen are novel and form an integral part of this invention.

Compounds of the formula XVI wherein $R_7$ is hydrogen and $R_9$ is methyl or n-butyl, and the ethyl and n-butyl esters of these compounds are reported in the literature (S. Oguchi, Nippon Kagaku Zasshi 86, 246 (1965); Chem. Abstracts 63:4295e).

Compounds of the formula XVI wherein X and Y are nitrogen and $R_7$ is hydrogen are prepared from compounds of the formula

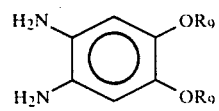

XVII by heating with dihydroxytartaric acid in a solvent such as water, or in a mixture of water and an organic solvent such as ethanol or dioxane.

Compounds of the formula XVII are prepared from compounds of the formula

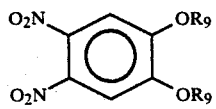

XVIII by methods of reduction well known in the art, such as hydrogenation in a solvent such as ethylacetate or ethanol over a catalyst such as platinum black or palladium on charcoal, or by treating with a reducing agent such as stannous chloride in a solvent such as ethyl acetate.

Compounds of the formula XVIII are either known or are prepared from known compounds of the formula

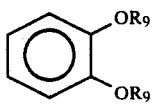

XIX by methods of nitration well known in the art (such as with fuming nitric acid in a solvent such as acetic acid).

Compounds of the formula I wherein X is nitrogen, Y is CH, and $R_7$ is hydrogen, or X is CH, Y is nitrogen and $R_7$ is hydrogen are prepared from compounds of the formula III wherein X is nitrogen, Y is CH, and $R_7$ is hydrogen, following procedures analogous to those used in the preparation of compounds of the formula I wherein both X and Y are nitrogen.

The compound of the formula III wherein X is nitrogen, Y is CH, and $R_7$ is hydrogen is prepared from the compound of the formula XV wherein X is nitrogen, Y is CH, and $R_7$ is hydrogen following procedures analogous to those used in the preparation of compounds of the formula III wherein both X and Y are nitrogen. The compound of the formula XV wherein X is nitrogen, Y is CH, and $R_7$ is hydrogen is prepared from the known compound 6,7-dimethoxyquinoline-2,3-dicarboxylic acid (S. B. Kadin, C. H. Lamphere J. Org. Chem. 49, 4999 (1984)) by methods of dealkylation well known in the art, such as heating with hydriotic acid or treatment with boron tribromide.

Compounds of the formula I wherein $R_7$ is chlorine or bromine can be prepared from compounds of the formula III wherein $R_7$ is chlorine or bromine following procedures analogous to those used in the preparation of compounds of the formula I wherein $R_7$ is hydrogen.

Compounds of the formula III wherein $R_7$ is chlorine or bromine can be prepared from compounds of the formula XV wherein $R_7$ is chlorine or bromine following procedures analogous to those used in the preparation of compounds of the formula III wherein $R_7$ is hydrogen.

Compounds of the formula XV wherein $R_7$ is chlorine or bromine can be prepared from compounds of the formula XVI wherein $R_7$ is chlorine or bromine following procedures analogous to those used in the preparation of compounds of the formula XV wherein $R_7$ is hydrogen.

Compounds of the formula XVI wherein $R_7$ is chlorine can be prepared from compounds of the formula XVI wherein $R_7$ is hydrogen by chlorination methods well known in the art (such as heating with sulfuryl chloride).

Compounds of the formula XVI wherein $R_7$ is bromine can be prepared from compounds of the formula XVI wherein $R_7$ is hydrogen by bromination procedures well known in the art (such as treatment with elemental bromine in a solvent such as acetic acid).

Compounds of the formula I wherein X and Y are nitrogen and $R_7$ is fluorine can be prepared from the compound of the formula III wherein X and Y are nitrogen and $R_7$ is fluorine following procedures analogous to those used in the preparation of compounds of the formula I wherein X and Y are nitrogen and $R_7$ is hydrogen.

The compound of the formula III wherein X and Y are nitrogen and $R_7$ is fluorine can be prepared from the compound of the formula XV wherein X and Y are nitrogen and $R_7$ is fluorine following procedures analogous to those used in the preparation of the compound of the formula III wherein X and Y are nitrogen and $R_7$ is hydrogen.

The compounds of the formula XV wherein X and Y are nitrogen and $R_7$ is fluorine can be prepared from compounds of the formula XVI wherein X and Y are nitrogen and $R_7$ is fluorine following procedures analogous to those used in the preparation of the compound of the formula XV wherein X and Y are nitrogen and $R_7$ is hydrogen.

Compounds of the formula XVI wherein X and Y are nitrogen and $R_7$ is fluorine can be prepared from compounds of the formula

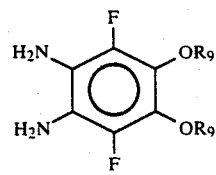

XX following procedures analogous to those used in the preparation of compounds of the formula XVI wherein X and Y are nitrogen and $R_7$ is hydrogen.

Compounds of the formula XX can be prepared from compounds of the formula

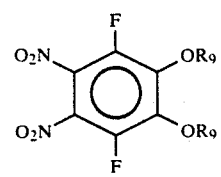

XXI following procedures analogous to those used in the preparation of compounds of the formula XVII.

Compounds of the formula XXI can be prepared from compounds of the formula

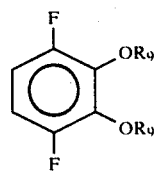

XXII following procedures analogous to those used in the preparation of compounds of the formula XVIII.

Compounds of the formula XXII can be prepared from a compound of the formula

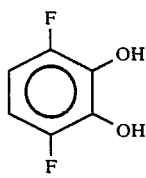
XXIII by methods of protection well known in the art (such as reaction with benzyl bromide and an acid acceptor; heating with acetic anhydride, or heating with acetone and an acid catalyst such as toluene sulfonic acid in the presence of a dehydrating agent such as molecular sieves).

The compounds of the formula XXIII can be prepared from the known compound 1,2-dimethoxy-3,6-difluorobenzene (see D. L. Ladd and J. Weinstock, *J. Org. Chem.* 46, 203, 1981) by methods of dealkylation well known in the art (such as treatment with boron tribromide).

Compounds of the formula I, wherein X is nitrogen, Y is CH and $R_7$ is fluorine or X is CH, Y is nitrogen and $R_7$ is fluorine can be prepared from compounds of the formula III wherein X is nitrogen, Y is CH and $R_7$ is fluorine using procedures analogous to those used in preparation of compounds of the formula I wherein X and Y are nitrogen and $R_7$ is hydrogen.

A compound of the formula III wherein X is nitrogen, Y is CH, and $R_7$ is fluorine can be prepared from a compound of the formula XV wherein X is nitrogen, Y is CH, and $R_7$ is fluorine using procedures analogous to those used in the preparation of a compound of the formula III wherein X and Y are nitrogen and $R_7$ is hydrogen.

A compound of the formula XV wherein X is nitrogen, Y is CH, and $R_7$ is fluorine can be prepared from a compound of the formula

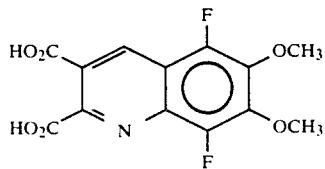
XXIV using methods of dealkylation well known in the art (such as heating with hydriotic acid or treatment with boron tribromide.

A compound of the formula XXIV can be prepared from compounds of the formula

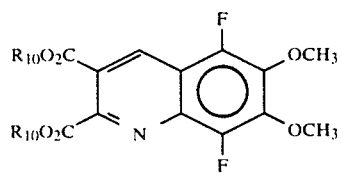
XXV wherein $R_{10}$ is lower alkyl (such as methyl or ethyl) by procedures well known in the art such as treatment with a strong base such as sodium hydroxide in a protic solvent such as water or methanol.

Compounds of the formula XXV can be prepared from compounds of the formula

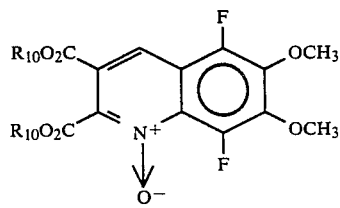
XXVI by methods well known in the art (such as heating with a reducing agent such as phosphorous trichloride in a non-protic solvent such as chloroform).

Compounds of the formula XXVI can be prepared by reacting a compound of the formula

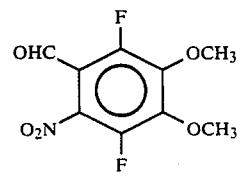
XXVII with known compounds of the formula

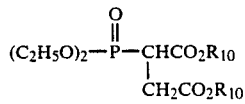
XXVIII in the presence of a lower alkoxide (such as sodium ethoxide) in a lower alkanol solvent (such as ethanol).

A compound of the formula XXVII can be prepared from a compound of the formula

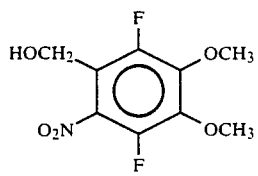
XXIX by oxidation methods well known in the art (such as chromium trioxide-pyridine complex in a solvent such as dichloromethane).

A compound of the formula XXIX can be prepared from a compound of the formula

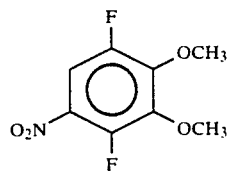
XXX by treatment with a strongly basic organometallic reagent (such as n-butyl lithium) followed by the addition of gaseous formaldehyde, in a solvent such as tetrahydrofuran or diethyl ether.

A compound of the formula XXX can be prepared from the previously cited known compound 1,2,-dimethoxy-3,6-difluorobenzene by methods of nitration well know in the art (such as treatment with concentrated nitric acid in a solvent such as acetic acid).

The compounds of formula 1 wherein $R_3$, $R_4$ and $R_7$ are hydrogen are the preferred compounds.

The compounds of formula I contain at least one chiral center-the carbon atom (in the 3-position of the β-lactam nucleus) to which the acylamino substituent is attached. This invention is directed to those β-lactams which have been described above, wherein the stereochemistry at the chiral center in the 3-position of the β-lactam nucleus is the same as the configuration at the carbon atom in the 6-position of naturally occurring penicillins (e.g., penicillin G) and as the configuration at the carbon atom in the 7-position of naturally occurring cephalosporins (e.g., cephalosporin C).

The compounds of formula I have the imino substituent

and can, therefore, exist as the syn or anti isomer or as a mixture of isomers. All of these isomeric forms are within the scope of this invention. In general, however, the syn isomer of a compound of formula I has the greatest activity.

The following examples are specific embodiments of this invention.

EXAMPLE 1

[2S-[2α,3β(Z)]]-2-[[[1-(2-Amino-4-thiazolyl)-2-[(2-methyl-4-oxo-1-sulfo-3-azetidinyl)amino]-2-oxoethylidene]amino]oxy]-2-methylpropanoic acid, 2-[(3-carboxy-6,7-dihydroxy-2-quinolinyl)carbonyl]hydrazide and

EXAMPLE 2

[2S-[2α,3β(Z)]]-2-[[[1-(2-Amino-4-thiazolyl)-2-[(2-methyl-4-oxo-1-sulfo-3-azetidinyl)amino]-2-oxoethylidene]amino]oxy]-2-methylpropanoic acid, 2-[(2-carboxy-6,7-dihydroxy-3-quinolinyl)carbonyl]hydrazide (A) 6,7-Dimethoxy-2,3-quinolinedicarboxylic acid A suspension of 26.7 g (80 mmol) of 6,7-dimethoxy-2,3-quinolinedicarboxylic acid, diethyl ester, prepared as described by S. B. Kadin and C. H. Lamphere, J. Org. Chem., 49, 4999 (1984), in 10% sodium hydroxide solution (containing 16 g (400 mmol) of sodium hydroxide) was refluxed for 5 hours. After the filtration of the hot solution, 300 ml of water and subsequently 3N hydrochloric acid were added until the pH reached 1.0. The solids were filtered off by suction, washed thoroughly with water, and dried in vacuo to give 22.4 g of the desired product having a melting point of 264°–266° C.

(B) 6,7-Dihydroxy-2,3-quinolinedicarboxylic acid

A suspension of 8.64 g (31.17 mmol) of 6,7-dihydroxy-2,3-quinolinedicarboxylic acid in 125 ml of aqueous hydrogen iodide solution (57%) was refluxed for 3 hours. After cooling, the precipitate was filtered off by suction, washed with water and dried in vacuo to give 4.7 g (60.5%) of desired acid with melting point > 300° C. 1H-NMR(DMSO): δ=7.32 (s,2H); 8.60 (s, 1H).

(C) 6,7-Dihydroxy-2,3-quinolinedicarboxylic anhydride

To a solution of 4.60 g (18.64 mmol) of 6,7-dihydroxy-2,3-quinolinedicarboxylic acid in 110 ml of dimethylformamide were added 4.19 g (20.31 mmol) of dicyclohexylcarbodiimide (DCC). After stirring overnight, the precipitate (dicyclohexylurea) was filtered off and the filtrate evaporated to dryness. The product thus obtained still contained diacid 6,7-dihydroxy-2,3-quinolinedicarboxylic acid so that the procedure was repeated with another 1.0 g of dicyclohexylcarbodiimide. After the evaporation of the filtrate to dryness, the residue was triturated with ethyl acetate. Filtration and evaporation of the ethyl acetate yielded 2.38 g. of the title compound (contains 1 mol equivalent of dimethylformamide). 1H-NMR(DMSO): δ=7.51 (s,1H); 7.52 (s,1H) 8.87 (s,1H).

(D) [2S-[2α,3β(Z)]]-2-[[[1-(2-Amino-4-thiazolyl)-2-[(2-methyl-4-oxo-1-sulfo-3-azetidinyl)amino]-2-oxoethylidene]amino]oxy]-2-methylpropanoic acid, 2-[(3-carboxy-6,7-dihydroxy-2-quinolinyl)carbonyl]hydrazide

[2S-[2α,3β(Z)]]-2-[[[1-(2-Amino-4-thiazolyl)-2-[(2-methyl-4-oxo-1-sulfo-3-azetidinyl)amino]-2-oxoethylidene]amino]oxy]-2-methylpropanoic acid, 2-[(2-carboxy-6,7-dihydroxy-3-quinolinyl)carbonyl]hydrazide A solution of 6,7-dihydroxyquinoline-2,3-dicarboxylic anhydride (485 mg, 2.4 mmole) in 10 ml of DMF at 25° C. was treated with a solution of [2S-[2α,3β(Z)]]-2-[[[1-(2-amino-4-thiazolyl)-2-[(2-methyl-4-oxo-1-sulfo-3-azetidinyl) amino]-2-oxoethylidene]amino]oxy]-2-methylpropanoic acid, hydrazide (prepared according to Example 12 of U.S. Pat. No. 4,610,824) (1.42 g, 2.10 mmole) in 10 ml of DMF followed by enough triethylamine to raise the pH to ~7.5 (650 mg, 6.5 mmole). The mixture was stirred for a total of 43 hours at 25° C., then evaporated to a residue. This material was taken up in water (pH=3.45), adjusted to pH 6.0 with $KHCO_3$, and passed through a column of Dowex AG50(K+) in water. The product was recovered by lyophilization and chromatographed on a 150 ml HP-20* column in water. Partial separation into a major component (358 mg) and a minor component (248 mg) was achieved.

The major component (358 mg) was taken up in water and adjusted to pH 3.7 with dilute hydrochloric acid. This turbid solution was chromatographed on a HP-20 column, giving 36 mg of impure minor component (eluting in water), 87 mg of major component (eluting in water), and 103 mg of major component (eluting in ~10% acetonitrile/water).

The minor component (248 mg) was dissolved in water and adjusted to pH=2.5 with dilute hydrochloric acid. The resulting gum was chromatographed on an HP-20 column in a 1:1 water:acetonitrile gradient. First to elute was 37 mg of minor component (~5% $CH_3CN/H_2O$), then 29 mg of a mixture, and finally 62 mg of the major component (~10% $CH_3CN/H_2O$).

Another 98 mg of minor component and 53 mg of major component were isolated by rechromatographing the mixed fractions. The total yield of the major component (Example 1)=305 mg.

IR(KBr): 1762 $cm^{-1}$ (CO). 1H-NMR ($D_2O+CD_3CO_2D$): δ=1.58 (d,3H); 1.66 (s,6H); 4.25 (m,1H); 4.71 (d,1H); 7.22 (s, 1H); 7.39 (s,1H); 7.41 (s, 1H); 8.70 (s, 1H). The total yield of minor component (Example 2)=135.

IR(KBr): 1763 $cm^{-1}$(CO). 1H-NMR (DMSO): δ=1.44 (d, 3H); 1.49 (s, 3H); 1.51 (s,3H); 3.74 (m, 1H); 4.59 (d,1H); 6.97 (s,1H); 7.25 (s,1H); 7.34 (s, 1H); 8.42 (s,1H).

*HP-20: Macroreticular styrene-divinylbenzene copolymer. Mitsubishi Chemical Industries, Ltd.

EXAMPLE 3

[2S-[2α,3β(Z)]]-2-[[[1-(2-Amino-4-thiazolyl)-2-[(2-methyl-4-oxo-1-sulfo-3-azetidinyl)amino]-2-oxoethylidene]amino]oxy]-2-methylpropanoic acid, 2-[(3-carboxy-6,7-dihydroxy-2-quinoxalin-2-yl)-carbonyl]hydrazide

EXAMPLE 3A

Preparation of 2,2-Dimethyl-1,3-benzodioxole

A mixture of catechol (55 g, 0.5 moles), acetone (150 ml), benzene (150 ml) and p-toluenesulfonic acid (15 mg) was refluxed in a Soxlet extractor containing 140 g of baked 4Å molecular sieves for 24 hours, as described in E. R. Cole, et al., Aust. J. Chem. 33, 675 (1980). The sieves were replaced with fresh sieves and refluxing continued for another 24 hours. The solvents were removed in vacuo and the residue was triturated with 1 liter of hexane. The light yellow solution was decanted and washed with 10% NaOH until the washes were colorless. The organic layer was dried ($Na_2SO_4$) and evaporated to 32.4 g (43%) of title compound as an oil which was used without further purification.

1H-NMR($CDCl_3$): $\delta = 1.73$ (s, 6H); 6.78 (s, 4H).

EXAMPLE 3B

Preparation of 2,2-Dimethyl-5-nitro-1,3-benzodioxole

A solution of 70% (conc.) nitric acid (20 ml) and glacial acetic acid (10 ml) cooled at 12° C. was treated by drops with 5 g (33.3 mmole) of the compound of Example 3A at a rate to maintain the temperature at 15°-20° C. Stirring was continued for 15 minutes after addition, then the brown slurry was diluted to 100 ml with water and filtered. The solid was washed with water, taken up in $CH_2Cl_2$, dried ($Na_2SO_4$) and evaporated to 5.40 g (83%) of pure yellow mononitro title compound.

1H-NMR($CDCl_3$): $\delta = 1.73$ (s, 6H); 6.72 (d,1H); 7.53 (m,1H); 7.78 (m, 1H).

EXAMPLE 3C

Preparation of 2,2-Dimethyl-5,6-dinitro-1,3-benzodioxole

A solution of 90% (fuming) nitric acid (22 ml) and glacial acetic acid (11 ml) cooled at 12° C. was treated in portions with solid compound from Example 3B (5.4 g, 27.7 mmoles) so as to maintain the temperature of <17° C. After the addition, stirring was continued for 15 minutes, when the internal temperature began to fall. The mixture was diluted to 100 ml with water, the yellow solid filtered, washed with water, taken up in $CH_2Cl_2$, dried ($Na_2SO_4$) and evaporated to give 5.43 g (82%) of pure title compound.

1H-NMR ($CDCl_3$): $\delta = 1.80$ (s,6H); 7.17 (s,2H).

EXAMPLE 3D

Preparation of 5,6-Diamino-2,2-dimethyl-1,3-benzo dioxole;dihydrochloride salt

A solution of compound from Example 3C (2.02 g, 8.42 mmole) in 100 ml of ethyl acetate was treated with 65 mg of platinum oxide and hydrogenated for 24 hours at 1 atmosphere. The catalyst was filtered and the filtrate treated with dry HCl in ethyl acetate to give a solid. This was filtered, washed with ethyl acetate and ether, and dried in vacuo to give 2.06 g (97%) of title compound which contained solvents of crystallization (~15% by weight).

1H-NMR($D_2O$); $\delta = 1.67$ (s, 6H); 6.77 (s, 2H).

EXAMPLE 3E

Preparation of 2,2-Dimethyl-1,3-dioxolo[4,5 g]-quinoxaline-6,7-dicarboxylic acid A solution of compound from Example 3D (1.56 g, 6.17 mmole) in 120 ml of water was treated with $NaHCO_3$ until pH=6.0, then treated with 1.85 g (8.19 mmoles) of solid dihydroxytartaric acid, disodium salt, hydrate. The resulting slurry was stirred and heated at 75° C. for 45 minutes, giving a clear yellow solution and a small amount of amorphous brown material. The mixture was cooled to 25° C., extracted with $CH_2Cl_2$ until the organic layer was colorless, then concentrated to 30 ml at 40° C. in vacuo. This solution was acidified to pH=2.35 and the resulting thick slurry chilled and filtered. Further concentration gave a second crop, for a total of 1.47 g (82%) of title compound on drying.

1H-NMR (DMSO): $\delta = 1.80$ (s,6H); 7.40 (s, 2H).
13C-NMR (DMSO): $\delta = 25.7$, 103.9, 121.6, 139.7, 143.2, 152,2, 166.2.

EXAMPLE 3F

Preparation of 6,7-Dihydroxyquinoxaline-2,3-dicarboxylic acid

Compound from Example 3E (145 mg, 0.5 mmole) was slurried in 10 ml of concentrated HCl and heated at 75° C. for 1 hour with stirring. On initial heating, the compound dissolved, then a precipitate eventually formed. The slurry was evaporated to dryness in vacuo. The residue was initially soluble in water but formed a yellowbrown precipitate within a few minutes. The water was evaporated again and the residue was dried in vacuo for 3 hours to give the title compound as a brown solid, 125 mg, m.p.>300° C.

1H-NMR (DMSO): $\delta = 7.27$ (s,2H).

EXAMPLE 3G

Preparation of [2S-[2α,3β(Z)]]-2-[[[1-(2-Amino-4-thiazolyl)-2-[(2-methyl-4-oxo-1-sulfo-3-azetidinyl)amino]-2-oxoethylidene]amino]oxy]-2-methylpropanoic acid, 2-[(3-carboxy-6,7-dihydroxy-2-quinoxalin-2-yl)carbonyl]hydrazide:

Compound from Example 3F (125 mg, 0.5 mmole) was dissolved in 4 ml of dry DMF and treated with 103 mg (0.5 mmole) of DCC in 0.5 ml of DMF at 25° C. After 1.25 hours a solution of [2S-[2α,3β(Z)]]-2-[[[1-(2-amino-4-thiazolyl)-2-[(2-methyl-4-oxo-1-sulfo-3-azetidinyl)-amino]-2-oxoethylidene]amino]-oxy]-2-methyl propanoic acid, hydrazide (prepared in Example 12 of U.S. Pat. No. 4,610,824) (282 mg, 0.42 mmole) in 3 ml of dry DMF was treated with 100 mg (1.0 mmole) of TEA and the basic (pH=9) solution added to the anhydride solution. After stirring at 25° C. for 3 hours the mixture was evaporated in vacuo. Water was added and the mixture (pH=3.65) adjusted to pH=6.10 with $KHCO_3$ and passed through a column of Dowex AG50(K+). The pooled product fractions were adjusted to pH=2.50 with HCl and the solution applied to a 75 ml HP-20 column. Eluting with a water: acetonitrile gradient gave the title compound, 128 mg (38%).

IR (KBr): 1760 cm$^{-1}$ (CO). 1H-NMR (DMSO): δ=1.44 (d, 3H); 1.51 (d, 6H); 3.72 (m, 1H); 4,56 (d, 1H); 6.95 (s, 1H); 7.30 (s,1H); 7.35 (s, 1H).

EXAMPLE 4

[2R-[2α,3α(Z)]]-2-[[[1-(2-Amino-4-thiazolyl)-2-[(2-methyl-4-oxo-1-sulfo-3-azetidinyl)amino]-2-oxoe-thylidene]amino]oxy]-2-methylpropanoic acid, 2-[(3-carboxy-6,7-dihydroxy-2-quinoxalin-2-yl)carbonyl]hydrazide

EXAMPLE 4A

Preparation of
[2R-[2α,3α(Z)]]-2-[[[1-(2-amino-4-thiazolyl)-2-[(2-methyl-4-oxo-1-sulfo-3-azetidinyl)amino]-2-oxoe-thylidene]amino]oxy]-2-methyl propanoic acid, 2-[1,1-dimethylethoxy)carbonyl]hydrazide, tetrabutyl ammonium salt A solution of 870 mg (2 mmoles) of [2R-[2α,3α(Z)]]-2-[[[1-(2-amino-4-thiazolyl)-2-[(2-methyl-4-oxo-1-sulfo-3-azetidinyl)amino]-2-oxoethylidene]amino]oxy]-2-methyl propanoic acid in 11 ml of dry dimethylformamide was treated with tributylamine (370 mg, 2 mmoles), N-hydroxybenzotriazole (40 mg), dimethylamino pyridine (20 mg) and 412 mg (2 moles) of dicylohexylcarbodiimide. After stirring for 45 minutes at 25° C. a solution of t-butylcarbazate (264 mg, 2 mmoles) in 2 ml of dimethylformamide was added. After stirring overnight, the resulting slurry was filtered and evaporated to dryness in vacuo. The residue was dissolved in 50 ml of acetone, filtered and treated with 680 mg (2 mmole) of potassium perfluorobutanesulfonate. The resulting slurry was diluted with ether, filtered and dried. Chromatography on HP-20 resin in water gave product fractions which were lyophilized, taken up in 50 ml of water, saturated with sodium sulfate, treated with 680 mg (2 mmoles) of tetrabutylammonium hydrogen sulfate and extracted with dichloromethane. Drying the extracts and evaporation gave the title compound as 885 mg of a hard foam.

EXAMPLE 4B

Preparation of
[2R-[2α,3α(Z)]]-2-[[[1-2-amino-4-thiazolyl)-2-[2-methyl-4-oxo-1-sulfo-3-azetidinyl)amino]-2-oxoe-thylidene]amino]oxy]-2-methyl-propanoic acid, hydrazide A solution of the compound of Example 4A (885 mg, 1.12 mmole) and anisole (2 ml) in 15 ml of dichloromethane at −10° C. was treated with 10 ml of trifluoroacetic acid and allowed to warm to +15° C. over two hours. Toluene (10 ml) was added and the volatiles were removed in vacuo. Trituration with ether gave 594 mg of the title compound as a nearwhite solid.

EXAMPLE 4C

Preparation of
[2R-[2α,3α(Z)]]-2-[[[1-(2-amino-4-thiazolyl)-2-[(2-methyl-4-oxo-1-sulfo-3-azetidinyl)amino]-2-oxoe-thylidene]amino]oxy]-2-methylpropanoic acid, 2-[(3-carboxy-6,7-dihydroxy-2-quinoxalin-2-yl)carbonyl]hydrazide A solution of 250 mg (1 mmole) of the compound of Example 3F in 10 ml of dimethylformamide was treated with 206 mg of dicylohexylcarbodiimide. After stirring for 1 hour at 25° C. the resulting slurry was treated with a mixture of the compound of Example 4B (522 mg, 0.77 mmole) and triethylamine (200 mg, 2 mmole) in 2 ml of dimethylformamide at 25° C. After stirring for 16 hours, the resulting slurry was filtered and evaporated in vacuo. The residue was dissolved in water and potassium bicarbonate to raise the pH to 6.05, then passed through an ion exchange resin [DOWEX AG50 (K+)]. The eluted product solution was acidified to pH 2.50 with dilute hydrochloric acid and chromatographed on HP-20 in a water-acetonitrile gradient. Product fractions were lyophilized to give the title compound as a yellow solid (202 mg).

IR (KBr): 1756 cm$^{-1}$ (CO). 1H-NMR (DMSO): δ=1.30 (d,3H); 1.51 (d, 6H); 4.07 (m, 1H); 5.13 (d, 1H); 7.02 (s, 1H); 7.30 (s, 1H); 7.36 (s,1H).

EXAMPLE 5

[2R-[2α,3α(Z)]]-[[[1-(2-Amino-4-thiazolyl)-2-[(2-methyl-4-oxo-1-sulfo-3-azetidinyl)amino]-2-oxoe-thylidene]amino]oxy]acetic acid, 2-[(3-carboxy-6,7-dihydroxy-2-quinoxolinyl)carbonyl]hydrazide

EXAMPLE 5A

Preparation of
[2R-[2α,3α(Z)]]-[[[1-(2-Amino-4-thiazolyl)-2-[(2-methyl-4-oxo-1-sulfo-3-azetidinyl)amino]-2-oxoe-thylidene]amino]oxy]acetic acid, diphenylmethyl ester, tetrabutyl ammonium salt.

A solution of 2R-[2α,3α]-3-amino-2-methyl-4-oxo-1-sulfo-azetidine (1.80 g 10 mmoles) with one equivalent of TEA (1.01 g, 10 mmoles) in 5 ml DMF was added to a solution of (Z)-2-amino-α-[[2-(diphenylmethoxy)2-oxoethoxy]-imino]-4-thiazoleacetic acid, 1H-benzotriazoly-1-yl ester (5.28 g, 10 mmoles) in 15 ml DMF at 20° C. The reaction remained at room temperature for 15 hours, before the solvent was removed in vacuo to give a yellow residue. The residue was taken up into 100 ml acetone and filtered through celite to remove white insoluble particles. A solution of potassium perfluorobutane sulfonate (3.38 g, 10 mmoles) in 15 ml of acetone was added to the filtrate, followed by 200 ml ether and 125 ml hexane which caused a white solid to form. The mixture was cooled to 0° C. for two hours before filtering and drying the solid in vacuo to give 6.08 g of an off white solid. This solid was dissolved in water (50 ml) and treated with 50 ml of a solution of 3.38 g (10 mmoles) of tetrabutylammonium hydrogensulfate which had been adjusted to pH=2.5 with sodium bicarbonate. The mixture was extracted with methylene chloride and the organic layer was dried (sodium sulfate) and evaporated to a foam. Crystallization from ethyl acetate gave 7.63 g of the title compound as a white solid.

IR(KBr): 1754 cm$^{-1}$ (CO). 1H-NMR (CDCl$_3$): δ=0.97 (t, 12H); 1.40 (m, 11H); 3.22 (m, 8H); 4.33 (m, 1H); 4.85 (m, 2H); 5.25 (m, 1H); 5.92 (s, 2H); 6.86 (s, 1H); 6.94 (s, 1H); 7.30 (s, 10H); 7.52 (d, 1H).

EXAMPLE 5B

Preparation of
[2R-[2α,3α(Z)]]-[[[1-(2-Amino-4-Thiazolyl)-2-[(2-methyl-4-oxo-1-sulfo-3-azetidinyl)amino]-2-oxoe-thylidene]amino]oxy]acetic acid To a slurry of the compound of Examples 5A (7.63 g, 8.2 mmoles) and 20 ml of anisole in 80 ml CH$_2$Cl$_2$ cooled to −15° C. was added 88 ml of cold TFA. The acid addition caused the solid to dissolve. After 30 minutes at −10° C., the solution was diluted with 150 ml of ethyl acetate which caused a white precipitate to form. The solid was filtered and dried to give 3.33 g of the title compound.

IR (KBr): 1745 cm$^{-1}$ (CO). 1H-NMR (D$_2$O): δ=1.33 (d, 3H); 4.46 (m, 1H); 4.82 (s, 2H); 5.29 (d, 1H); 7.14 (s, 1H).

Example 5C

Preparation of [2R-[2α,3α(Z)]]-[[[1-(2-Amino-4-Thiazolyl)-2-[2-methyl-4-oxo-1-sulfo-3-azetidinyl)amino]-2-oxoethylidene]amino]oxy]acetic acid, 2-[1,1-dimethylethoxy)carbonyl]hydrazide, tetrabutylammonium salt The compound of Example 5B (10.02 g, 24.6 mmoles) was slurried in 25 ml of methylene chloride at room temperature. The addition of tributylamine (4.56 g, 24.6 mmoles) caused the solid to dissolve. Dimethylamino pyridine (0.005 g, 0.04 mmoles), N-hydroxybenzotriazole monohydrate (0.005 g, 0.03 mmoles) and t-butylcarbazate (3.89 g, 29.5 mmoles) were added to the solution followed by a solution of dicyclohexyl carbodiimide (5.08 g, 24.6 mmoles) in 10 ml of methylene chloride. The immediate rise in reaction temperature was quickly arrested with cooling in ice, and after ½ hour the cooling bath was removed. At this point TLC indicated that starting material was still present, so another 2.04 g (9.89 mmoles) of DCC in 5 ml of methylene chloride was added. When TLC after one hour indicated that starting material was still present, a third portion of DCC was added (1.0 g, 4.85 mmoles) and the reaction was complete as shown on TLC by the absence of starting material. After stirring another ½ hour the solution was filtered through celite and the solvent removed in vacuo to give a yellow foam. The foam was taken up in 75 ml of acetone, filtered, and then treated with a solution of potassium perfluorobutanesulfonate (8.31 g, 24.6 mmoles) in 40 ml of acetone. The resulting white solid was filtered, then taken up in 200 ml of water and treated with a solution of tetrabutylammonium hydrogen sulfate (8.41 g, 24.6 mmoles) in 75 ml of water which had been adjusted to pH=2.5 with potassium bicarbonate. The solution was extracted with 3×200 ml of methylene chloride and the organic layers were combined and dried over sodium sulfate. Evaporation gave yellow foam. The foam was dissolved in 200 ml of acetone and diluted with 350 ml of ethyl acetate to the cloud point and allowed to stand overnight at room temperature. The resulting light yellow solid was scratched and in another two hours filtered to give 10.24 g, 54.6% yield of the title compound which was clean by TLC and high field NMR.

IR (KBr): 1760 cm$^{-1}$ (CO). 1H-NMR (D$_2$O): δ=0.92 (t, 12H); 1.40 (m, 22H); 1.60 (m, 8H); 4.42 (m, 1H); 4.73 (s, 2H); 5.31 (d, 1H); 7.00 (s, 1H).

EXAMPLE 5D

Preparation of [2R-[2α,3α(Z)]]-[[[1-(2-Amino-4-Thiazolyl)-2-[(2-methyl-4-oxo-1-sulfo-3-azetidinyl)amino]-2-oxoethylidene]amino]oxy]acetic acid, hydrazide, trifluoroacetate salt The compound of Example 5C (8.72 g, 16.8 mmoles) and 6 ml anisole were slurried in 100 ml CH$_2$Cl$_2$ at −15° C. A slow addition of 40 ml TFA to the mixture was followed by stirring for 4 hours at 0° C., when the reaction no longer showed starting material by TLC. Ethyl acetate (75 ml) was added to the reaction and the resulting slurry was filtered to give a white solid, 6.12 g after drying in vacuo.

IR (KBr): 1751 cm$^{-1}$ (CO). 1H-NMR (D$_2$O): δ=1.27 (d, 3H); 4.40 (m, 1H); 4.84 (s, 2H); 5.24 (d, 1H); 7.12 (s, 1H).

EXAMPLE 5E

Preparation of [2R-[2α,3α(Z)]]-[[[1-(2-Amino-4-thiazolyl)-2-[(2-methyl-4-oxo-1-sulfo-3-azetidinyl)amino]-2-oxoethylidene]amino]oxy]acetic acid, 2-[(3-carboxy-6,7-dihydroxy-2-quinoxolinyl)carbonyl]hydrazide A solution of dicyclohexylcarbodiimide (0.12 g, 0.6 mmoles) in 5 ml dimethylformamide (DMF) was added to a solution of the compound of Example 3F (0.15 g 0.6 mmoles) in 5 ml DMF at 0° C. The reaction was followed by TLC, indicating after 45 minutes dicylohexylcarbodiimide no longer remained. A solution of the compound from Example 5D (0.40 g, 0.60 mmoles) and triethylamine (TEA) (0.12 g, 1.2 mmoles) in 5 ml DMF was added to the anhydride, with additional TEA to raise the solution pH to 7–8. The reaction was stirred at room temperature for 15 hours before filtering and removing the solvent in vacuo to give a yellow residue. The residue was taken up into water and the pH raised to 6.1 with potassium bicarbonate solution before loading onto a column of Dowex AG50 (K$^+$). Elution with water and lyophilization of the pertinent fraction gave 0.90 g of a yellow solid. The solid was taken into water, the pH lowered to 2.1 with dilute hydrochloric acid and the solution loaded onto a 200 ml Hp-20 column. Elution with water was followed by a gradient of H$_2$O/CH$_3$CN,1/1. The collected fractions were placed at 5° C. for 18 hours where upon a yellow solid had formed in several fractions. These fractions were combined, centrifuged and filtered to give 0.011 g of the title compound of a yellow solid (2.2% yield). The supernatant from the solid and other fractions containing desired material were combined and lyophilized to give 0.080 g of the title compound as a yellow solid, 20% yield.

IR(KBr): 1751 cm$^{-1}$ (CO). 1H-NMR (DMSO): δ=1.26 (d, 3H; 4.07 (m, 1H); 4.77 (m, 2H); 4.88 (m, 1H) 7.03 (s, 1H); 7.31 (s, 1); 7.37 (s, 1H); 9.55 (d, 1H); 10.02 (s, 1H); 10.74 (s, 1H).

EXAMPLE 6

[2S-[2α,3β(Z)]]-2-[[[1-(2-Amino-4-thiazolyl)-2-[(2-methyl-4-oxo-1-sulfo-3-azetidinyl)amino]-2-oxoethylidene]amino]oxy]-2-methylpropanoic acid, 2-[(3-carboxy-5,8-dichloro-6,7-dihydroxy-2-quinoxalinyl)carbonyl]hydrazide, tripotassium salt

EXAMPLE 6A

Preparation of 4,9-Dichloro-1,3-dioxolo[4,5-g]-quinoxaline-6,7-dicarboxylic acid The compound of Example 3E, (860 mg, 2.97 mmole) was slurried in 15 ml of glacial acetic acid and treated with 15 ml of sulfuryl chloride. The mixture was heated at 65° C. for 2.5 hours, treated with another 6 ml of sulfuryl chloride, and heated for another 1.5 hours. The volatiles were removed in vacuo to give 830 mg (78%) of title compound as a yellow solid.

1H-NMR (DMSO): δ=1.91 (s, 2H) 13C-NMR (DMSO): s=25.7, 106.7, 125.1, 136.7, 142.7, 149.4, 165.9.

EXAMPLE 6B

Preparation of 5,8-Dichloro-6,7-dihydroxy quinoxaline-2,3-dicarboxylic acid

The compound of Example 6A (359 mg, 1.0 mmole) was slurried in concentrated HCl and heated to 70° C. for 11 hours. The volatile components of the resulting slurry were removed in vacuo, water was added and evaporated three times. The resulting solid was dissolved in DMF and evaporated, taken up in acetonitrile and evaporated twice and finally azotroped with benzene to give the title compound as an orange solid which contains some of compound of Example 6A as judged by TLC and C-13 NMR. 13C-NMR (DMSO): δ=112.9, 134.5, 142.3, 149.7, 166.2.

EXAMPLE 6C

[2S-[2α,3β(Z)]-2-[[[1-(2-Amino-4-thiazolyl)-2-[2-methyl-4-oxo-1-sulfo-3-azetidinyl)amino]-2-oxoethylidene]amino]oxy]-2-methylpropanoic acid, 2-[(3-carboxy-5,8-dichloro-6,7-dihydroxy-2-quinoxalinyl)carbonyl]hydrazide, tripotassium salt A solution of the entire crude sample of the compound of Example 6b [prepared from the hydrolysis of 359 mg, (1.0 mmole) of the compound of Example 6A] in 8 ml of dry DMF at 25° C. was treated with 185 mg (0.9 mmole) of DCC in 2 ml of DMF and the nearly black mixture allowed to stir at this temperature for 1 hour. A solution of [2S-[2α, 3β (Z)]]-2-[[[1-(2-amino-4-thiazolyl)-2-[(2 -methyl-4-oxo-1-sulfo-3-azeridinyl)amino]-2-oxoethylidene]amino]oxy-2-methyl-propanoic acid, hydrazide (600 mg, 0.89 mmoles) in 3 ml of DMF was treated with 200 mg (2 mmoles) of TEA and the mixture (pH=8) added to the black anhydride mixture. The resulting orange-red slurry was stirred under argon at 25° C. for 14 hours. The mixture was evaporated in vacuo, slurried in water and the pH adjusted to 6.0 with KHCO$_3$. The mixture was passed through a plug of Dowex AG50 (K+), and the pH of the eluant adjusted to 2.0 with dilute HCl. Chromatography on HP-20 with a water and acetonitrile gradient gave 320 mg of product, impure by TLC. A second purification in water at pH=5.0 gave 266 mg, still impure by HPLC. A third chromatography of 200 mg of the above crude product on a mixed bed (95% Amberchrom AD 16 1.5% Amberlite CG50) column buffered at pH=5.1 and eluted with water gave incomplete separation and pronounced tailing. The combined product fractions from the third chromatography (162 mg) were taken up in water, adjusted to pH 6.8 with potassium bicarbonate and chromatographed on the same mixed bed column, now buffered as pH=6.8. Lyophilization of the purest product fractions resulted in 80 mg (12.2%) of title compound as a bright yellow solid. IR(KBr): 1764 cm$^{-1}$ (CO). 1H-NMR (D$_2$O): δ=1.60 (d, 3H); 1.644 (s, 3H); 1.648 (s, 3H), 4.31 (m, 1H); 7.05 (s, 1H); 13C-NMR (D$_2$O): δ=17.9, 24.7, 59.5, 62.3, 66.6, 84.9, 1009.8, 110.0, 115.2, 133.0, 135.3, 138.5, 141.3, 146.7, 150.7, 165.6, 165.8, 166.8, 172.1, 175.2, 177.1.

EXAMPLE 7

6,7-Dihydroxy-2,3-quinoxalinedicarboxylic acid, 2-[[2R-[2α,3α(Z)]]-2-[2-[[[1-(2-amino-4-thiazolyl)-2-[(2-methyl-4-oxo-1-sulfo-3-azetidinyl)-amino]-2-oxoethylidene]amino]oxy]-2-methyl-1-oxopropyl]-2-methylhydrazide], dipotassium salt

EXAMPLE 7A

Preparation of 1-(benzyloxy)carbonyl-1-methylhydrazine

A solution of methylhydrazine (42.5 ml, 0.8 mole) and triethylamine (224 ml, 1.6 mole) in 700 ml of tetrahydrofuran at 0° C. was treated dropwise with benzylchloroformate (114 ml, 0.8 mole), then allowed to stir at ambient temperature overnight. The volatiles were evaporated and the residue was partitioned between water and ethyl acetate. Insoluble material was filtered. The organic phase was washed with water, dried over magnesium sulfate and evaporated. The residue was triturated with 1 L. of diethyl ether, the solution decanted and evaporated to an oil. The oil was dissolved in 200 ml of a mixture of methanol and 25 ml of concentrated hydrochloric acid. The volatiles were removed in vacuo and the residue was crystallized from a mixture of ethanol and ethylacetate to give 22.0 g of the hydrochloride of the title compound as colorless crystals. This material was dissolved in water and the pH was adjusted to 9.0. Extraction with ethyl acetate, drying over magnesium sulfate and the evaporation gave 19.0 g of the title compound as a colorless oil.

1H-NMR (CDCl$_3$): δ=3.00 (s, 3H); 4.68 (s, broadened, 2H); 5.12 (s, 2H); 7.10 (m, 5H).

EXAMPLE 7B

Preparation of 1-(benzyloxy)carbonyl-2-(t-butyloxy) carbonyl-1-methylhydrazine

A solution of the compound of Example 7A (15.8 g, 87 mmole), di-t-butyl-dicarbonate (24.0 g, 110 mmole) and dimethylaminopyridine (10 mg) in 40 ml of acetonitrile and 40 ml of water was heated at 60° C. for 48 hours. The volatile materials were evaporated and the residue was dissolved in ethyl acetate. Washing with 0.1 m citric acid, drying over magnesium sulfate and evaporation gave crude title compound which was chromatographed on silica gel in a mixture of ethyl acetate and cyclohexane to give 15.0 g of pure title compound of a colorless solid, mp 60°-65° C.

IR (Film): 1700 cm$^{-1}$(s); 3270 cm$^{-1}$ (m). 1H-NMR (DMSO); δ=1.38 (s, 9H); 3.03 (s, 3H); 5.10 (s, 2H); 7.35 (s, 5H); 9.35 (s, 1H).

EXAMPLE 7C

Preparation of 1-(t-butyloxy)carbonyl-2-methyl hydrazine

A mixture of the compound of Example 7B (15.0 g, 53 mmole), methanol (100 ml), concentrated hydrochloric acid (4.9 ml), and 10% palladium-on-charcoal (3.0 g) was hydrogenated for 1 hour at 1 atm. The mixture was filtered and evaporated, and the residue dissolved in water. The pH was raised to 8.0. Extraction with ethylacetate yielded the title compound 5.6 g, m.p. 50° C.

IR(KBr): 760 cm$^{-1}$(m), 1705 cm$^{-1}$(s), 2986 cm$^{-1}$(s). 1H-NMR (CDCl$_3$): δ=1.48 (s, 9H); 2.65 (s, 3H); 6.30 (s, br, 1H).

EXAMPLE 7D

1-[2-[(1,3-Dihydro-1,3-dioxo-2H-isoindol-2-yl)oxy]-2-methyl-1-oxopropyl]-2-[(t-butyloxy)carbonyl]-1-methylhydrazide 2-[(1,3-Dihydro-1,3-dioxo-2H-isoindol-2-yl)oxy]-2-methylpropanoyl chloride (5.3 g, 22 mmole) in 40 ml of dry tetrahydrofuran (THF) at 0° C. was treated with triethylamine (4.1 ml, 30 mmole) and 5 mg of dimethylaminopyridine followed by the dropwise addition of the compound of Example 7C (2.90 g, 20 mmole) in 20 ml of THF. The mixture was stirred overnight at ambient temperature and the volatiles then were evaporated. The residue was partitioned between ethyl acetate and water. The organic layer was washed sequentially with 0.5N hydrochloric acid, dilute bicarbonate, and water, dried over magnesium sulfate, and evaporated to give the title compound as a solid, 6.6 g, m.p. 140°–145° C.

EXAMPLE 7E

Preparation of
1-[2-Aminooxy)-2-methyl-1-oxopropyl]-2-[(t-butyloxy)carbonyl]-1-methylhydrazide A solution of the compound of Example 7D (7.10 g, 19 mmole) in dichloromethane (50 ml) at 0° C. was treated dropwise with hydrazine hydrate (1.80 ml, 38 mmole). After 30 minutes the mixture was filtered and the filtrate evaporated. Crystallization from ether/petroleum ether mixture gave the title compound as a colorless solid, 3.8 g, m.p. 85°–90°.

IR (KBr): 2990 cm$^{-1}$(m), 1735 cm$^{-1}$ (s), 1635 cm$^{-1}$ (s). 1H-NMR (DMSO): $\delta = 1.25$ (s, 6H); 1.42 (s, 9H); 2.95 (s, br, 3H); 5.83 (s, br, 2H); 9.25 (s, br, 1H).

EXAMPLE 7F

Preparation of
(Z)-[(2-Amino-4-thiazolyl)-α-[1,1-dimethyl-2-[2-(t-butyloxy)carbonyl-1-methylhydrazino]-2-oxoethoxy]imino]acetic acid.

To a solution of 2-amino-4-thiazole glyoxylic acid (1.72 g, 10 mmole) in 25 ml of dimethylformamide (DMF) at 25° C. was added a solution of the compound of Example 7E (2.47 g, 10 mmole) in 10 ml of DMF. After stirring overnight at 25° C., the volatile materials were evaporated in vacuo and the residue crystallized from ether to give the title compound, 3.3 g, m.p. 145° C.

IR (KBr): 1730 cm$^{-1}$ (s), 1655 cm$^{-1}$ (s). 1H-NMR (DMSO): $\delta = 1.42$ (s, 15H); 2.92 (s, br, 3H); 6.75 (s, 1H); 7.20 (s, br, 2H).

EXAMPLE 7G

Preparation of
1-[[2R-[2α,3α(Z)]]-2-[2-[[[1-(2-amino-4-thiazolyl)-2-[(-2-methyl-4-oxo-1-sulfo-3-azetidinyl)-amino]-2-oxoethylidene]amino]oxy]-2-methyl-1-oxopropyl]]-2-[(t-butyloxy)carbonyl]-1-methylhydrazine A solution of the compound of Example 7F (2.00 g, 5 mmole) in 40 ml of DMF was cooled to 0° C. and treated with N-hydroxybenzotriazole monohydrate (0.76 g, 5.0 mmole) and dicyclohexylcarbodiimide (1.23 g, 6.0 mmole). After 10 minutes a solution of 2R-[2α,-3α]-3-amino-2-methyl-4-oxo-1-sulfoazetidine (0.83 g, 5.0 mmole) and triethylamine (0.70 ml, 5.0 mmole) in 20 ml of DMF was added and the mixture stirred at ambient temperature overnight. Filtration and evaporation gave an oily residue which was dissolved in acetone, filtered and treated with the potassium salt of perfluorobutanesulfonic acid (1.9 g, 5.5 mmole). The resulting slurry was diluted with ether, filtered and chromatographed on a reversed-phase column (Organogen) in water containing 10% acetonitrile. Lyophilization gave the title compound as a solid, 1.4 g, m.p. 210°–240° C.

IR(KBr): 1765 cm$^{-1}$ (CO). 1H-NMR (DMSO): $\delta = 1.25$ (d, 3H); 1.40 (s, 9H); 1.43 (d, 6H); 2.95 (s, br, 3H); 4.05 (m, 1H); 5.10 (d, 1H); 7.05 (s, 1H).

EXAMPLE 7H

Preparation of
1-[[2R-[2α,3α(Z)]]-2-[2-[[[1-(2-amino-4-thiazolyl)-2-[(2-methyl-4-oxo-1-sulfo-3-azetidinyl)-amino]-2-oxoethylidene]amino]oxy]-2-methyl-1-oxopropyl]]-1-methylhydrazine, monotrifluoroacetic acid salt The compound of Example 7G (1.10 g, 1.83 mmole) was added to 45 ml of trifluoroacetic acid at 0° C. After 3 hours at this temperature the volatiles were evaporated in vacuo and the residue triturated with ether to give the title compound as colorless crystals, 1.34 g.

IR (KBr): 1760 cm$^{-1}$ (CO). 1H-NMR (DMSO/TFA): $\delta = 1.25$ (d, 3H); 1.60 (d, 6H); 3.35 (s, 3H); 4.05 (m, 1H); 5.07 (m, 1H); 7.05 (s, 1H).

EXAMPLE 7I

Preparation of 6,7-Dihydroxy-2,3-quinoxaline dicarboxylic acid,2-[[2R-[2α,3α(Z)]]-2-[2-[[[1-(2-amino-4-thiazolyl)-2-[(2-methyl-4-oxo-1-sulfo-3-azetidinyl)-amino]-2-oxoethylidene]amino]oxy]-2-methyl-1-oxopropyl]-2-methylhydrazide], dipotassium salt A solution of the compound of Example 3F (0.48 g, 1.92 mmole) in 10 ml of DMF at 0° C. was treated with dicylohexylcarbodiimide (0.47 g, 2.36 mmole), and stirred for 4 hours, then filtered N-Methyl-N-(trimethylsilyl) trifluoroacetamide (1.0 g, 5.0 mmole) was added and after 30 minutes the volatiles were removed in vacuo. The residue was taken up in 10 ml of DMF, chilled to 0° C., and treated with a solution of the compound of Example 7H (1.34 g, 1.83 mmole), triethylamine (0.57 g, 5.60 mmole) and N,N-dimethylaminopyridine (5 mg) in 5 ml of DMF. After stirring at ambient temperature overnight, the volatiles were removed in vacuo and the residue was dissolved in water, filtered and the pH adjusted to 6.0 with potassium bicarbonate. This solution was stirred with an ion-exchange resin Dowex 50 WX-8 for 30 minutes, filtered and chromatographed on a reversed-phase column (Organogen) in water to give the title compound, 0.39 g.

IR(KBr): 1660 cm$^{-1}$ (CO). 1H-NMR (DMSO,TFA): $\delta = [1.10(s,2H), 1.24$ (s, 1H)]; 1.60 (d, 3H); [3.10 (s, 2H); 3.32 (s, 1H)]; [3.80 (s, 2/3H), 4.10 (s, 1/3 H)]; [5.00 (s, 2/3H), 5.10 (s, 1/3H)]; [7.00 (s, 2/3 H), 6.90 (s, 1/3H)]; 7.32 (s, 1H); 7.39 (s, 1H).

EXAMPLE 8

6,7-Dihydroxy-2,3-quinoxalinedicarboxylic acid, 2-[[2S-[2α,3β(Z)]]-2-[2-[[[1-(2-amino-4-thiazolyl)-2-[(2-methyl-4-oxo-1-sulfo-3-azetidinyl-amino]-2-oxoethylidene]amino]oxy]-2-methyl-1-oxopropyl]-1-methylhydrazide], disodium salt

EXAMPLE 8A

Preparation of 1-[(t-butyloxy)carbonyl]-1-methylhydrazine

Di-t-butyl-dicarbonate (10.91 g, 50 mmole) was added to a solution of methyl hydrazine (2.3 g, 50 mmole) in 100 ml of tetrahydrofuran and 100 ml of water. The pH of the mixture was maintained at 8–9 with 2N sodium hydroxide, and the solution stirred overnight at this pH. The organic solvent was removed in vacuo and the aqueous residue was extracted with ethyl acetate. The organic layer was dried over sodium sulfate, concentrated and distilled in vacuo to give the title compound as an oil, 3.68 g.

IR (film): 1695 cm$^{-1}$ (CO). 1H-NMR (DMSO): δ=1.40 (s, 9H); 2.90 (s, 3H); 4.47 (s, 2H).

EXAMPLE 8B

Preparation of 2-[[2S-[2α,3β(Z)]]-2-[2-[[[1-(2-amino-4-thiazolyl)-2-[(2-methyl-4-oxo-1-sulfo-3-azetidinyl)-amino]-2-oxoethylidene]amino]oxy]-2-methyl-1-oxopropyl]]-1-[(t-butyloxy)carbonyl]-1-methylhydrazine A solution of [2S-[2α,3β(Z)]]-2-[[[1-(2-amino-4-thiazolyl)-2-[(2-methyl-4-oxo-1-sulfo-3-azetidinyl)amino]-2-oxoethylidene]amino]oxy]-2-methylpropanoic acid (aztreonam, 2.18 g, 5.0 mmole), tributylamine (0.93 g, 5.0 mmole), 1-hydroxybenzotriazole monohydrate (0.80 g, 5.0 mmole), N,N-dimethylaminopyridine (60 mg, 0.5 mmole) and dicylohexylcarbodiimide (1.13 g, 5.5 mmole) in 50 ml of DMF was stirred for 30 minutes, then was treated with the compound of Example 8A (0.73 g, 5.0 mmole) and the resulting mixture was stirred for three days at ambient temperature. The mixture was filtered and the volatiles evaporated in vacuo. The residue was dissolved in 20 ml of acetone and treated with 1.70 g (5 mmole) of the potassium salt of perfluorobutanesulfonic acid. The resulting slurry was diluted with ether and filtered. Chromatography on a reversed-phase column (XAD) in a water-acetonitrile gradient gave the title compound, 390 mg.

IR(KBr): 1760 cm$^{-1}$(CO). 1H-NMR (DMSO): δ=1.3–1.55 (m, 18H); 2.91 (s, 3H); 3.70 (m, 1H); 4.55 (m, 1H); 6.80 (s, 1H); 7.29 (s, br, 2H); 9.22 (d, 1H); 9.65 (s, 1H).

EXAMPLE 8C

Preparation of 2-[[2S-[2α,3β(Z)]]-2-[2-[[[1-(2-amino-4-thiazolyl)-2-[(2-methyl-4-oxo-1-sulfo-3-azetidinyl)-amino]-2-oxoethylidene]amino]oxy]-2-methyl-1-oxopropyl]]-1-methylhydrazine, monotrifluoroacetic acid salt.

To a mixture of the compound of Example 8B (1.15 g, 1.96 mmole) and anisole (2 ml) at 0° C. was added trifluoroacetic acid (20 ml). After stirring for one hour at 0° C. the volatiles were evaporated in vacuo and the residue triturated with ether. The resulting solid was filtered and dried in vacuo to give the title compound, 1.07 g.

IR (KBr): 1770 cm$^{-1}$ (CO). 1H-NMR (DMSO): δ=1.35–1.50 (m, 9H); 2.71 (s, 3H); 3.73 (m, 1H); 4.45 (m, 1H); 6.87 (s, 1H); 9.30 (d, 1H); 10.52 (s, br, 1H).

EXAMPLE 8D

Preparation of 6,7-Dihydroxy-2,3-quinoxalinedicarboxylic acid, 2-[[2S-[2α,3β(Z)]]-2-[2-[[[1-(2-amino-4-thiazolyl)-2-[(2-methyl-4-oxo-1-sulfo-3-azetidinyl)-amino]-2-oxoethylidene]amino]oxy]-2-methyl-1-oxopropyl]-1-methylhydrazide] disodium salt A mixture of the compound of Example 3F (0.26 g, 1.0 mmole) and dicyclohexylcarbodiimide (0.206 g, 1.0 mmole) in 10 ml of DMF was stirred at ambient temperatures for 2 hours, then was treated with a solution of the compound of Example 8 C (0.519 g, 0.9 mmole) and triethylamine (0.233 g, 2.3 mmole) in DMF (6 ml). The resulting mixture was stirred overnight at ambient temperature, filtered and the volatiles removed in vacuo. The residue was taken up in water and the pH was raised to 6.2 with 3N sodium hydroxide. Then the solution was filtered and stirred with 10 g of ion-exchange resin [Dowex 50 WX8 (Na$^+$)]. The resin was filtered and the filtrate was adjusted to pH=2.5 with 3N hydrochloric acid. The solution was lyophilized, redissolved in water, filtered and chromatographed on a reversed-phase column (XAD) in a mixture of water and acetonitrile (9:1). This product was converted to the sodium salt with ion-exchange resin and chromatographed as the salt on a reversed-phase column (Organogen) in water, to give the title compound, 50 mg, m.p.>300° C.

IR(KBr): 1760 cm$^{-1}$ (CO). 1H-NMR(DMSO+TFA): δ=0.8–1.6 (m, 9H); 3.07+3.17 (s, 3H); 3.72 (m, 1H); 4.55 (d, 1H); 7.00+7.13 (s, 1H); 7.26+7.29 (s, 1H); 7.27+7.35 (s, 1H).

What is claimed is:

1. Compounds of the formula

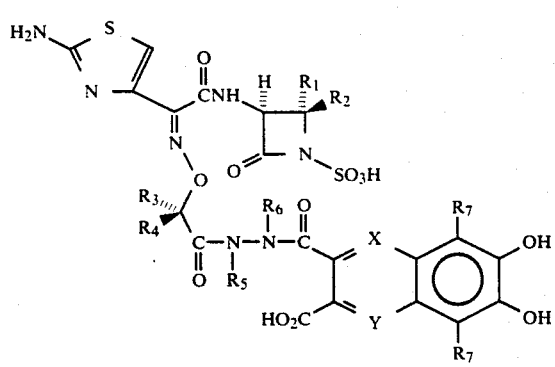

and pharmaceutically acceptable salts thereof, wherein R$_1$ and R$_2$ are the same or different and each is hydrogen, alkyl, alkenyl, alkynyl, cycloalkyl, phenyl, substituted phenyl or a 4, 5, 6 or 7-membered heterocycle or one of R$_1$ and R$_2$ is hydrogen and the other is azido, halomethyl, dihalomethyl, trihalomethyl, alkoxycarbonyl, —CH$_2$X$_1$; wherein X$_1$ is azido, amino, hydroxy, carboxy, alkoxycarbonyl, alkanoylamino, phenylcarbonylamino, (substituted phenyl)carbonylamino, alkylsulfonyloxy, phenylsulfonyloxy, (substituted phenyl)sulfonyloxy, phenyl, substituted phenyl, cyano,

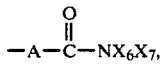

—S—$X_2$, or —O—$X_2$ (wherein A, $X_2$, $X_6$ and $X_7$ are as hereinafter defined); —S—$X_2$ or —O—$X_2$; wherein $X_2$ is alkyl, substituted alkyl, phenyl, substituted phenyl, phenylalkyl, (substituted phenyl)alkyl, alkanoyl, substituted alkanoyl, phenylalkanoyl, (substituted phenyl)alkanoyl, phenylcarbonyl, (substituted phenyl)carbonyl, or heteroarylcarbonyl; and in the case of when $X_1$ is —O—$X_2$ then $X_2$ can also be alkylideneamino, alkanoylamino, carboxyalkylideneamino, alkylsulphonylamino, alkoxycarbonylalkylsulphonylamino or N,N-cyclodialkanoylamino,

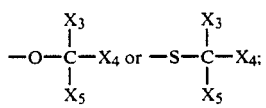

wherein one of $X_3$ and $X_4$ is hydrogen and the other is hydrogen or alkyl, or $X_3$ and $X_4$ when taken together with the carbon atom to which they are attached form a cycloalkyl groups, and $X_5$ is formyl, alkanoyl, phenylcarbonyl, (substituted phenyl)carbonyl, phenylalkylcarbonyl, (substituted phenyl)alkylcarbonyl, carboxyl, alkoxycarbonyl, aminocarbonyl, (substituted amino)carbonyl, or cyano, or

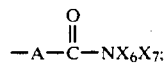

wherein A is —CH=CH—, —(CH$_2$)$_m$—, —(CH$_2$)$_m$—O—, —(CH$_2$)$_m$—NH—, or —CH$_2$—S—CH$_2$—, m is 0, 1 or 2, and $X_6$ and $X_7$ are the same or different and each is hydrogen, alkyl, phenyl or substituted pheny, or $X_6$ is hydrogen and $X_7$ is amino, substituted amino, alkanoylamino or alkoxy, or $X_6$ and $X_7$ when taken together with the nitrogen atom to which they are attached form a 4, 5, 6 or 7-membered heterocycle;

$R_3$ and $R_4$ are the same or different and each is hydrogen or alkyl or $R_3$ and $R_4$ taken together with the carbon atom to which they are attached are cycloalkyl;

$R_5$ and $R_6$ are the same or different and each is hydrogen or alkyl or $R_5$ and $R_6$ taken together with the nitrogen atoms to which they are attached form a 1,2-diazacylobutane, 1,2-diazacyclopentane, 1,2-diacyclohexane, or 1,2-diazacycloheptane ring;

$R_7$ is hydrogen, fluorine, chlorine or bromine;

X is a nitrogen atom or CH;

Y is a nitrogen atom or CH;

provided that either X or Y is always a nitrogen atom.

wherein the term "substituted alkyl" refers to alkyl groups substituted with azido, amino, halogen, hydroxy, carboxy, cyano, alkoxycarbonyl, aminocarbonyl, alkanoyloxy, alkoxy, phenyloxy, (substituted phenyl)oxy, mercapto, alkylthio, phenylthio, (substituted phenyl)thio, alkylsulfinyl or alkylsulfonyl groups;

the term "substituted phenyl" refers to a phenyl group substituted with 1, 2 or 3 amino, halogen, hydroxyl, trifluoromethyl, alkyl of 1 to 4 carbon atoms, alkoxy of 1 to 4 carbon atoms, alkanoyloxy, aminocarbonyl, or carboxy groups;

the term "substituted amino" refers to a group having the formula —N$X_8X_9$ wherein $X_8$ is hydrogen, alkyl, phenyl, substituted phenyl, phenylalkyl or (substituted phenyl)alkyl, and $X_9$ is alkyl, phenyl, substituted phenyl, phenylakyl, (substitutedphenyl)alkyl, hydroxy, cyano, alkoxy, phenylalkoxy or amino;

the term "heteroaryl" refers to pyridinyl, furanyl, pyrrolyl, thienyl, 1,2,3-triazolyl, 1,2,4-triazolyl, imdazolyl, thiazolyl, thiadiazolyl, pyrimidinyl, oxazolyl, triazinyl, teterazol, tetrazolyl or one of the above groups substituted with one or more halogen, hydroxy, nitro,amino, cyano, trifluoromethyl, alkyl of 1 to 4 carbon atoms, alkoxy of 1 to 4 carbon atoms, alkylsulfonyl, phenyl, substituted phenyl, 2-furfurylideneamino, benzylideneamino, or substituted alkyl wherein the alkyl group has 1 to 4 carbon atoms, groups;

the term "a 4,5,6 or 7-membered heterocycle" refers to pyridinyl, furanyl, pyrrolyl, thienyl, 1,2,3-triazolyl, 1,2,4-triazolyl, imidazolyl, thiazolyl, thiadiazolyl, pyrimidinyl, oxazolyl, triazinyl, tetrazolyl, azetinyl, oxetanyl, thietanyl, piperidinyl, piperazinyl, imidazolylidinyl, oxazolidinyl, pyrrolidinyl, tetrahydropyrimidinyl, dihydrothiazolyl or hexahydroazepinyl or one of the above groups substituted with one or more oxo, halogen, hydroxy, nitro, amino, cyano, trifluoromethyl, alkyl of 1 to 4 carbon atoms, alkoxy of 1 to 4 carbon atoms, alkylsulfonyl, phenyl, substituted phenyl, 2-furfurylideneamino, benzylideneamino, or substituted alkyl wherein the alkyl groups has 1 to 4 carbon atom, groups.

2. A compound according to claim 1 wherein X and Y are nitrogen.

3. A compound according to claim 1 wherein X or Y is CH and the other is nitrogen.

4. A compound according to claim 1 wherein X is nitrogen and Y is CH.

5. A compound according to claim 1 wherein X is CH and Y is nitrogen.

6. A compound according to claim 1 wherein $R_1$ is hydrogen and $R_2$ is alkyl.

7. A compound according to claim 1 wherein $R_1$ is alkyl and $R_2$ is hydrogen.

8. A compound according to claim 1 wherein $R_3$ and $R_4$ are methyl.

9. A compound according to claim 1 wherein $R_3$ and $R_4$ are the same or different and each is hydrogen or alkyl.

10. A compound according to claim 1 wherein $R_3$ is hydrogen and $R_4$ is methyl.

11. A compound according to claim 1 wherein $R_3$ is methyl and $R_4$ is hydrogen.

12. A compound according to claim 1 wherein $R_3$ and $R_4$ are hydrogen.

13. A compound according to claim 1 wherein $R_5$ and $R_6$ are the same or different and each is hydrogen or alkyl.

14. A compound according to claim 1 wherein $R_5$ and $R_6$ are hydrogen.

15. A compound according to claim 1 wherein $R_5$ is hydrogen and $R_6$ is methyl.

16. A compound according to claim 1 wherein $R_5$ is methyl and $R_6$ is hydrogen.

17. A compound according to claim 1 wherein $R_7$ is hydrogen.

18. A compound according to claim 1 wherein $R_7$ is chlorine.

19. A compound according to claim 1, [2S-[2α,3β(Z)]]-2-[[[1-(2-amino-4-thiazolyl)-2-[(2-methyl-4-oxo-1-sulfo-3-azetidinyl)amino]-2-oxoethylidene]amino]oxy]-2-methylpropanoic acid, 2-[(3-carboxy-6,7-dihydroxy-2-quinolinyl)carbonyl]-hydrazide.

20. A compound according to claim 1, [2S-[2α,3β(Z)]]-2-[[[1-(2-amino-4-thiazolyl)-2-[(2-methyl-4-oxo-1-sulfo-3-azetidinyl)amino]-2-oxoethylidene]amino]oxy]-2-methylpropanoic acid, 2-[(2-carboxy-6,7-dihydroxy-3-quinolinyl)carbonyl]hydrazide.

21. A compound according to claim 1, [2S-[2α,3β(Z)]]-2-[[[1-(2-amino-4-thiazolyl)-2-[(2-methyl-4-oxo-1-sulfo-3-azetidinyl)amino]-2-oxoethylidene]amino]oxy]-2-methylpropanoic acid, 2-[(3-carboxy-6,7-dihydroxy-2-quinoxalin-2-yl)carbonyl]hydrazide.

22. A compound according to claim 1, [2R-[2α,3α(Z)]]-2-[[[1-(2-amino-4-thiazolyl)-2-[(2-methyl-4-oxo-1-sulfo-3-azetidinyl)amino]-2-oxoethylidene]amino]oxy]-2-methylpropanoic acid, 2-[(3-carboxy-6,7-dihydroxy-2-quinoxalin-2-yl)carbonyl]hydrazide.

23. A compound according to claim 1, [2R-[2α,3α(Z)]]-[[[1-(2-amino-4-thiazolyl)-2-[(2-methyl-4-oxo-1-sulfo-3-azetidinyl)amino]-2-oxoethylidene]amino]oxy]acetic acid, 2-[(3-carboxy-6,7-dihydroxy-2-quinoxolinyl)carbonyl]hydrazide.

24. A compound according to claim 1, [2S-[2α,3β(Z)]]-2-[[[1-(2-amino-4-thiazolyl)-2-[(2-methyl-4-oxo-1-sulfo-3-azetidinyl)amino]-2-oxoethylidene]amino]oxy]-2-methylpropanoic acid, 2-[(3-carboxy-5,8-dichloro-6,7-dihydroxy-2-quinoxalinyl)carbonyl]hydrazide.

25. A compound according to claim 1, 6,7-dihydroxy-2,3-quinoxalinedicarboxylic acid, 2-[[2R-[2α,3α (Z)]]-2-[2-[[[1-(2-amino-4-thiazolyl)-2-[(2-methyl-4-oxo-1-sulfo-3-azetidinyl)-amino]-2-oxoethylidene]amino]oxy]-2-methyl-1-oxopropyl]-2-methylhydrazide].

26. A compound according to claim 1, 6,7-dihydroxy-2,3-quinoxalinedicarboxylic acid, 2-[[2S-[2α,3β(Z)]]-2-[2-[[[1-(2-amino-4-thiazolyl)-2-[(2-methyl-4-oxo-1-sulfo-3-azetidinyl)-amino]-2-oxoethylidene]amino]oxy]-2-methyl-1-oxopropyl]-1-methylhydrazide].

* * * * *